(12) United States Patent
Coller et al.

(10) Patent No.: US 7,790,362 B2
(45) Date of Patent: Sep. 7, 2010

(54) CONTROLLED PLATELET ACTIVATION TO MONITOR THERAPY OF ADP ANTAGONISTS

(75) Inventors: Barry S. Coller, New York, NY (US); Dennis Durbin, Solana Beach, CA (US)

(73) Assignee: Accumetrics, Inc., San Diego, CA (US)

( * ) Notice: Subject to any disclaimer, the term of this patent is extended or adjusted under 35 U.S.C. 154(b) by 0 days.

(21) Appl. No.: 10/886,155

(22) Filed: Jul. 6, 2004

(65) Prior Publication Data
US 2005/0031616 A1 Feb. 10, 2005

Related U.S. Application Data

(60) Provisional application No. 60/485,703, filed on Jul. 8, 2003.

(51) Int. Cl.
*C12Q 1/00* (2006.01)
(52) U.S. Cl. ......................................................... 435/4
(58) Field of Classification Search ................. None
See application file for complete search history.

(56) References Cited

U.S. PATENT DOCUMENTS

| | | | |
|---|---|---|---|
| 3,518,057 A | 6/1970 | Giordano | |
| 3,694,161 A | 9/1972 | Kleszynski et al. | |
| 4,051,236 A * | 9/1977 | Harris et al. | 424/532 |
| 4,066,360 A | 1/1978 | Breddin | |
| 4,820,836 A * | 4/1989 | Mori et al. | 548/512 |
| 5,023,233 A * | 6/1991 | Nutt et al. | 514/11 |
| 5,455,228 A | 10/1995 | Coller et al. | |
| 5,854,005 A | 12/1998 | Coller | |
| D409,758 S | 5/1999 | Warden et al. | |
| 5,922,551 A * | 7/1999 | Durbin et al. | 435/7.21 |
| 5,989,578 A * | 11/1999 | Bernat et al. | 424/422 |
| 6,016,712 A | 1/2000 | Warden et al. | |
| 6,043,871 A | 3/2000 | Solen et al. | |
| 6,063,847 A | 5/2000 | Chackalamannil et al. | |
| 6,210,904 B1 * | 4/2001 | Bednar et al. | 435/7.1 |
| 6,326,380 B1 | 12/2001 | Chackalamannil et al. | |
| 6,555,064 B2 | 4/2003 | Baugh et al. | |
| 6,645,987 B2 | 11/2003 | Chackalamannil et al. | |
| 6,894,065 B2 | 5/2005 | Chackalamannil et al. | |
| 7,037,920 B2 | 5/2006 | Chackalamannil et al. | |
| 7,205,115 B2 | 4/2007 | McHugh et al. | |
| 7,244,730 B2 | 7/2007 | Suzuki et al. | |
| 7,304,083 B2 | 12/2007 | Suzuki et al. | |
| 2006/0246527 A1 | 11/2006 | McHugh et al. | |
| 2006/0246528 A1 | 11/2006 | Swaim et al. | |
| 2007/0243632 A1 | 10/2007 | Coller et al. | |
| 2008/0299587 A1 | 12/2008 | Durbin | |

FOREIGN PATENT DOCUMENTS

| | | |
|---|---|---|
| WO | WO-98/41868 | 9/1998 |
| WO | WO 00/25140 | 5/2000 |
| WO | WO-2005/007868 | 1/2005 |

OTHER PUBLICATIONS

International Search Report for PCT/USO4/21785, mailed on Jun. 13, 2005, 4 pages.
Written Opinion of the International Searching Authority for PCT/USO4/21785, mailed on Jun. 13, 2005, 4 pages.
Angiolillo et al., "Functional Effects of High Clopidogrel Maintenance Dosing in Patients With Inadequate Platelet Inhibition on Standard Dose Treatment" The American Journal of Cardiology Online (Dec. 17, 2007) DOI: 10.1016/j.amcard.2007.09.087.
Behan et al., Platelets (2005) 16(2):73-80 (Abstract only).
Fox et al., Cell Calcium (2004) 35:39-46.
Gurbel et al., Journal of the American College of Cardiology (2007) 50(19):1822-1834.
Kim et al., Circ. J. (2007) 71:1867-1872.
McLean and Cannon, Critical Pathways in Cardiology (2006) 5:103-113.
Mclean and Cannon, Future Cardiol. (2006) 2:255-267.
Savi and Herbert, Seminars in Thrombosis and Hemostasis (2005) 31:174-183.
Storey et al., Thromb. Haemost. (2002) 88(3):488-494 (Abstract only).
Storey et al., Thromb. Res. (2005) 115(4):301-307 (Abstract only).
U.S. Appl. No. 11/742,684, filed May 1, 2007.
U.S. Appl. No. 11/411,239, filed Apr. 24, 2006.
Preliminary Amendment for U.S. Appl. No. 11/411,239, faxed on Aug. 16, 2006.
Preliminary Amendment for U.S. Appl. No. 11/411,239, faxed on Oct. 24, 2006.

(Continued)

*Primary Examiner*—Lora E Barnhart
(74) *Attorney, Agent, or Firm*—Cooley, LLP

(57) ABSTRACT

A method is provided of determining whether an individual has reduced ability to form platelet thrombi. An ADP platelet activator and one or platelet inhibitors are provided. At least one of the platelet inhibitors is Prostaglandin E1 (PGE1). An alternate signal transduction pathway is produced. A final concentration of ADP is 2 to 35 µM and a final concentration of PGE1 is 2 to 30 nM, preferably 20 to 25 nM.

18 Claims, 2 Drawing Sheets

OTHER PUBLICATIONS

Response to Notice of Non-Compliant Amendment for U.S. Appl. No. 11/411,239, filed Nov. 16, 2006.
U.S. Appl. No. 12/114,498, filed May 2, 2008.
Ahn et al., Bioorg. Med. Chem. Lett. (1999) 9:2073-2078.
Bernatowicz et al., J. Med. Chem. (1996) 39:4879-4887.
Coughlin, PNAS USA (1999) 96:11023-11027.
Covic et al., Biochemistry (2000) 39:5458-5467.
Covic et al., Thromb. Haemost. (2002) 87:722-727.
Hoekstra et al., Bioorg. Med. Chem. Lett. (1998) 8:1649-1654.
Hung et al., J. Biol. Chem. (1992) 267:20831-20834.
Hung et al., J. Clin. Invest. (1992) 89:1350-1353.
Kahn et al., J. Clin. Invest. (1999) 103:879-887.
Kahn et al., Nature (1998) 394:690-694.
Kay et al., Stroke (2007) 38(12):3259-3265.
Kogushi et al., J. Thromb. Haemost. (2007) 5(Suppl. 1):P-M-059.
MacFarlane et al., Pharmacol. Rev. (2001) 53:245-282.
Maryanoff et al., Curr. Med. Chem. Cardiovasc. Hematol. Agents (2003) 1(1):13-36.
McComsey et al., Bioorg. Med. Chem. Lett. (1999) 9:255-260.
O'Donnell et al., Stroke (2008) 39:1638-1646 (published online before print on Mar. 27, 2008).
Soslau et al., J. Biol. Chem. (2001) 276(24):21173-21183.
Vassallo et al., J. Biol. Chem. (1992) 267:6081-6085.
Vu et al., Cell (1991) 64:1057-1068.
Vu et al., Nature (1991) 353:674-677.
Xu et al., PNAS USA (1998) 95:6642-6646.
Angiolillo et al., European Heart Journal (2008) doi:10.1093/eurheartj/ehn287.
Boeynaems et al., Seminars in Thrombosis and Hemostasis (2005) 31(2):139-149.
Cattaneo, Seminars in Thrombosis and Hemostasis (2005) 31(2):168-173.
Curtin et al., "Clopidogrel and Ticlopidine" Chapter 51 in Platelets, Michelson, ed., Academic Press (2002), pp. 787-801.
Gachet and Hechler, Seminars in Thrombosis and Hemostasis (2005) 31(2):162-167.
Geiger et al., Arteriosclerosis, Thrombosis, and Vascular Biology (1999) 19:2007-2011.
Hechler et al., Seminars in Thrombosis and Hemostasis (2005) 31(2):150-161.
Ikeda et al., "Cilostazol" Chapter 53 in Platelets, Michelson, ed., Academic Press (2002), pp. 817-823.
Jacobson et al., Seminars in Thrombosis and Hemostasis (2005) 31(2):205-216.
Jakubowski et al., Thromb. Haemost. (2008) 99:409-415.
Jarvis et al., British Journal of Pharmacology (2000) 129:275-282.
Marcus et al., Seminars in Thrombosis and Hemostasis (2005) 31(2):234-246.
Nessel, Seminars in Thrombosis and Hemostasis (2005) 31(2):248.
Niitsu et al., Seminars in Thrombosis and Hemostasis (2005) 31(2):184-194.
Packham and Mustard, Seminars in Thrombosis and Hemostasis (2005) 31(2):129-138.
Packham, Thrombosis and Haemostasis (1983) 50(2):610-619.
Price et al., European Heart Journal (2008) doi:10.1093/eurheartj/ehn046.
Robson et al., Seminars in Thrombosis and Hemostasis (2005) 31(2):217-233.
Savi and Herbert, Seminars in Thrombosis and Hemostasis (2005) 31(2):174-183.
Shim et al., International Journal of Cardiology (2008) doi:10.1016/j.ijcard.2008.02.016.
Smyth and Fitzgerald, Vitamins and Hormones (2002) 65:149-165.
Van Giezen and Humphries, Seminars in Thrombosis and Hemostasis (2005) 31(2):195-204.
Varenhorst et al., European Society of Cardiology (2008) Abstract: P2597.
Varenhorst et al., "Assessment of P2Y12 inhibition with the point-of-care device VerifyNow® P2Y12 in patients treated with prasugrel or clopidogrel co-administered with aspirin" manuscript submitted Apr. 29, 2008 to the European Heart Journal.
Walenga and Hoppensteadt, Seminars in Thrombosis and Hemostasis (2005) 31(2):247.
Wang et al., Thrombosis Research (1992) 65(6):757-768.
Non-Final Office Action from U.S. Appl. No. 11/411,239, mailed on Jun. 25, 2008.
Amendment in Response to Non-Final Office Action from U.S. Appl. No. 11/411,239, filed Sep. 25, 2008.
Restriction Requirement from U.S. Appl. No. 11/119,360, mailed on Nov. 17, 2005.
Response to Restriction Requirement from U.S. App. No. 11/119,360, filed on Dec. 15, 2005.
Non-Final Office Action from U.S. App. No. 11/119,360, mailed on Jan. 12, 2006.
Response to Office Action from U.S. Appl. No. 11/119,360, filed Jul. 12, 2006.
Final Office Action from U.S. Appl. No. 11/119,360, mailed on Sep. 12, 2006.
Request for Continued Examination from U.S. Appl. No. 11/119,360, filed on Nov. 8, 2006.
Notice of Allowance from U.S. Appl. No. 11/119,360, mailed on Dec. 13, 2006.
First Preliminary Amendment from U.S. Appl. No. 12/114,498, filed Aug. 18, 2008.
U.S. Appl. No. 60/060,076, filed by Gandola et al. on Jun. 9, 2008.
Beer et al., Blood (1992) 79(1):117-128.
Gurbel et al., Journal of the American College of Cardiology (2005) 46(10):1827-1832.
International Search Report and Written Opinion for PCT/US2008/062297, mailed Aug. 6, 2008, 9 pages.
Cuisset et al., Am. J. Cardiol. (2008) 1700-1703.
Marcucci et al., Circulation (2009) 119:237-242.
Patti et al., JACC (2008) 52(14):1128-1133.
Supplemental European Search Report in PCT/US2004/021785; dated Jul. 17, 2009; 2 pages.
Smith, et al; "Rapid Platelet-Function Assay"; downloaded from circ.ahajournals.org; pp. 620-625 (Feb. 9, 1999).
Steinhubl, et al; "Point-of-Care Measured Platelet Inhibition Correlates With A Reduced Risk Of An Adverse Cardiac Event After Percutaneous Coronary Intervention"; downloaded from circ.ahajournals.org; pp. 2572-2578.

* cited by examiner

CONTROLLED PLATELET ACTIVATION TO MONITOR THERAPY OF ADP ANTAGONISTS

CROSS-REFERENCE TO RELATED APPLICATION

This application claims the benefit of U.S. Ser. No. 60/485,703, filed Jul. 8, 2003, which application is fully incorporated herein.

BACKGROUND OF THE INVENTION

1. Field of the Invention

This invention relates to the field of diagnostic assays, and in particular to the determination of platelet function activity on blood samples to study effects of anti-platelet compositions, and more particularly the dual use of a platelet activator (like ADP) and a platelet inhibitor (like Prostaglandin E1 (PGE1)) for measurement of platelet function of P2Y12 inhibitors, including clopidogrel, CS-747 (Sankyo), and ticlopidine with increased sensitivity.

2. Description of the Related Art

The role of platelets in mammalian physiology is extraordinarily diverse, but their primary role is in promoting hemostasis. In many situations, an evaluation of the ability of blood to clot is desired, a parameter that is frequently controlled by the ability of platelets to adhere and/or aggregate. Of interest, therefore, is the assessment of the adhesive functions of platelets. For example, questions of interest include whether to administer drugs that will block, or promote, clot formation, or whether to detect deficiencies in platelet function prior to surgical procedures. Also of interest is evaluating the effectiveness of a platelet inhibitor that is being tested as a new drug or is being used as approved clinical treatment in a patient.

Platelets are known to aggregate under a variety of conditions and in the presence of a number of different reagents. Platelet aggregation is a term used to describe the binding of platelets to one another. Platelet aggregation in vitro depends upon the ability of platelets to bind fibrinogen to their surfaces after activation by an aggregation-inducing agent such as ADP or collagen.

Platelets play a critical role in the maintenance of normal hemostasis. When exposed to a damaged blood vessel, platelets will adhere to exposed sub-endothelial matrix. Following the initial adhesion, various factors released or produced at the site of injury such as thrombin, ADP and collagen activate the platelets. Once platelets are activated, a conformational change occurs in the platelet glycoprotein GPIIb/IIIa receptor, allowing it to bind fibrinogen and/or von Willebrand factor.

It is this binding of the multivalent fibrinogen and/or von Willebrand factor molecules by GPIIb/IIIa receptors on adjacent platelets that results in the recruitment of additional platelets to the site of injury and their aggregation to form a hemostatic plug or thrombus.

In vitro platelet aggregometry is the laboratory method used to assess the in vivo ability of platelets to form the aggregates leading to a primary hemostatic plug. In this technique an aggregating agent such as ADP or collagen is added to whole blood or platelet-rich plasma and aggregation of platelets monitored. Platelet aggregometry is a diagnostic tool that can aide in patient diagnosis and selection of therapy. Current assays to measure platelet aggregation are expensive, time-consuming, cumbersome, and generally not suitable for a clinical environment.

A rapid platelet function assay has recently been developed and is described in U.S. Pat. No. 5,763,199 (Coller). The assay determines glycoprotein (GP)IIb/IIIa receptor blockade in whole blood. Agglutination of small polymeric beads coated with a GPIIb/IIIa ligand such as fibrinogen results when the beads are contacted with whole blood containing platelets with activated GPIIb/IIIa receptors that are not blocked. Failure to agglutinate indicates either failure of the GPIIb/IIIa receptors to become activated and/or blockade of the GPIIb/IIIa receptors. In a preferred embodiment, the addition of a thrombin receptor activator results in an assay that is rapid and convenient enough to be performed at the bedside and that results in agglutination of the small polymeric beads within a convenient, known period of time if the GPIIb/IIIa receptors are not blocked. The assay includes the ability to transfer blood to be tested from a collection container to an assay device without opening the collection container. This platelet aggregation assay can be conducted at the same time as the activated clotting time (ACT), which is performed to assess the adequacy of heparinization.

Platelet aggregation plays a key role in the pathogenesis of thrombosis and acute coronary artery disease. Evidence suggests that significant platelet function variability exists in the response to various antiplatelet agents. It has also been demonstrated that an inter-individual variability in platelet aggregation exists when P2Y12 antagonists such as clopidogrel are used for treatment of patients to achieve an anti-aggregation effect. The results of one study demonstrated that at least 10% of patients receiving the drug did not achieve the expected platelet aggregation inhibition (Muller I, Besta F, Schulz C, Massberg S, Schonig A, Gawaz M; Prevalence of clopidogrel non-responders among patients with stable angina pectoris scheduled for elective coronary stent placemen Thromb Haemost. 2003 May, 89(5):783-7).

Clopidogrel and ticlopidine are thienopyridine derivatives that inhibit platelet aggregation. They are believed to inhibit the binding of adenosine-5-diphosphate (ADP) to one of its receptors, the P2Y12 receptor. The pharmacological activity of clopidogrel is very similar to the pharmacological activity of ticlopidine. However, clopidogrel has been shown to have fewer side-effects than ticlopidine. Based on mounting evidence of the efficacy of clopidogrel in thrombotic disease, the use of clopidogrel and other P2Y12 antagonists are likely to increase significantly.

Since many patients with cardiovascular disease are currently taking one of the thienopyridine agents, a method for detection of resistance to a thienopyridine and assessment of the efficacy of thienopyridine treatment would be beneficial. Thus, there is a need to develop an assay that would provide information about aspirin and thienopyridine, e.g., clopidogrel or ticlopidine, sensitivity and efficacy of treatment in a given patient.

The effects of these agents on platelet function have been assessed with platelet aggregometry using ADP, collagen or other platelet activators. However, since ADP activates at least two different receptors (P2Y1 and P2Y12 and perhaps P2X1), it has the potential for lower specificity and background noise. Collagen is another choice. However collagen is highly variable due its quaternary structure, which dramatically affects it ability to activate platelets and due to the fact it is derived from biological tissue and sensitive to minor changes in temperature and pH. Neither collagen nor ADP provide specificity to the P2Y12 receptor and therefore by themselves are not the optimal choice for the determination of the effects of P2Y12 inhibitors. In particular as has been shown in several studies, the choice of concentration of these two agonists has significant effect on the degree of inhibition to P2Y12 antagonists that is measured.

Prostaglandins (PGs) belong to a ubiquitous class of chemicals known as eicosanoids. They are found in virtually every tissue in the body and have a very wide spectrum of biological activities. Eicosanoids are derivatives of arachidonic acid, a polyunsaturated fatty acid. The term eicosanoids includes the family of prostaglandins (PGs), prostacyclin, thromboxanes, and leukotrienes. The PGs are divided in different families depending on their structure, each designated by a letter (A, E, F, G, H, or I). In addition to this letter, each individual prostaglandin carries a digit that indicates the number of double bonds in its fatty acid side chain. For example, prostaglandin E1 (PGE1) belongs to the E family and has only one double bond in its side chain. PGs plays an important role in platelet aggregation and hemostasis (blood clotting) and typically have a marked vasodilator effect.

PGE1 is the theoretical cyclooxygenase metabolite of dihomo-γ-linolenic acid (DGLA), but it is virtually undetectable in the plasma of normal humans or other animals. Its pharmacology includes vasodilation, hypotension, and antiplatelet activities. PGE1 has been shown to inhibit platelet aggregation by increasing cyclic adenosine monophosphate (cAMP) concentrations within platelets. A number of groups have shown that the IC50 of PGE1 for the inhibition of ADP-induced human platelet aggregation is around 40 nM.

SUMMARY OF THE INVENTION

Accordingly an object of the present invention is to provide methods and kits for conducting an assay for platelet function activity on a blood sample.

Another object of the present invention is to provide methods and kits to assay a blood sample that has been affected by a P2Y12 antagonist measured by using a combination of ADP and PGE1 as the activator.

These and other objects of the present invention are achieved in a method of determining whether an individual has reduced ability to form platelet thrombi due to inhibition of platelet activation initiation, signal transduction and/or GPIIb/IIIa blockade. A blood sample is obtained from the individual being assessed. The blood sample is mixed in combination with 1) an anticoagulant; 2) sufficient buffer to maintain the pH and salt concentration of the anticoagulated blood within a range suitable for platelet aggregation; 3) a platelet GPIIb/IIIa receptor ligand immobilized on a solid surface; 4) one or more agents to enhance a signal transduction pathway and 5) a receptor activator. The combination is incubated under conditions for agglutinating particles. Platelet-mediated agglutination is assessed in the agitated mixture. The absence of agglutination indicates that the individual has a reduced ability to form platelet thrombi.

In another embodiment of the present invention, a kit is provided that includes an anticoagulant, and a buffer to maintain the pH and salt concentration of the anticoagulated blood within a range suitable for platelet aggregation. Also provided is a platelet GPIIb/IIIa receptor ligand immobilized on a solid surface, and a receptor activator with additional agents to enhance a signal transduction pathway.

In another embodiment of the present invention, a method is provided of determining whether an individual has reduced ability to form platelet thrombi due to inhibition of platelet activation initiation, signal transduction and/or GPIIb/IIIa blockade using controlled activation of the platelet. A platelet activator and one or platelet inhibitors are provided. An alternate signal transduction pathway is produced.

In another embodiment of the present invention, a kit is provided that includes a platelet GPIIb/IIIa receptor ligand immobilized on a solid surface, one or more agents to enhance a signal transduction pathway and a receptor activator.

DETAILED DESCRIPTION OF THE INVENTION

Figure 1:
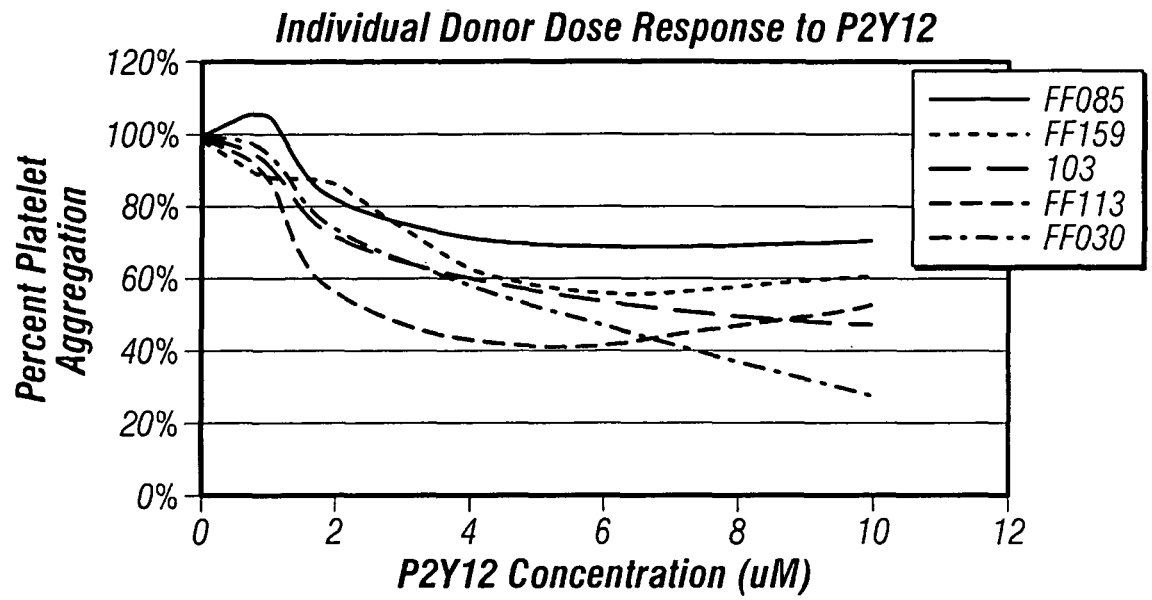
FIG. 1 illustrates the mean response of one individual.

In various embodiments of the present invention, a composition of ADP and PGE1 is utilized as an activator in measuring inhibition of platelet aggregation by P2Y12 antagonists such as thienopyridines in whole blood samples. Accordingly, the aforementioned compositions may be employed to determine the effectiveness of anti-platelet therapy involving treatment of patients with a thienopyridine. The above compositions may be employed in conjunction with particles coated with a GPIIb/IIIa receptor ligand and any other reagents necessary for conducting an assay for the efficacy of thienopyridines. A lyophilized reagent composition may be used that comprises the aforementioned activator composition and particles. In one approach, a metered volume of a sample to be measured such as whole blood is mechanically mixed with the lyophilized reagent. A change in light transmission is monitored and an index of platelet activity is calculated. In one aspect a whole blood sample is combined in a cuvette or a unitized cartridge with the aforementioned lyophilized reagent. An apparatus may be employed for carrying out the assay. The apparatus comprises a well for receiving the sample where the well contains the lyophilized reagent and other reagents for conducting the assay. The additional reagents may be various buffers and/or lyophilization stabilizers.

As mentioned above, in one aspect the present invention is directed to a method for conducting an assay for platelet function activity on a whole blood sample. In one embodiment, the sample is one that has been affected by an adenosine-5-phosphate (ADP) antagonist. For example, the sample may be from a patient undergoing treatment with by an adenosine-5-phosphate (ADP) antagonist. In the present invention a combination is provided in an assay medium where the combination comprises the sample and a composition of ADP and PGE1. Usually, the final concentration of ADP is 2 to 35 µM, preferably, 15 to 20 µM and the final concentration of PGE1 is 2 to 30 nM, preferably 20 to 25 nM.

Also employed in the present methods is a reagent comprising particles coated with a compound that can result in the specific agglutination of platelets, i.e., the agglutination of platelets by the specific interaction between a receptor on the platelets and the compound on the particles. Such compounds include, by way of illustration and not limitation, antibodies to a platelet receptor and GPIIb/IIIa receptor ligands, which may be a small organic molecule, polypeptide, protein, monoclonal antibody or nucleic acid that binds, complexes or interacts with GPIIb/IIIa receptors on the platelet surface. Platelet mediated aggregation of the particles results when the GPIIb/IIIa receptors on the surface of platelets bind, complex or otherwise interact with the GPIIb/IIIa receptor ligands on the particles. Typical GPIIb/IIIa ligands include fibrinogen, monoclonal antibody 10E5 (Coller, et al., J. Clin. Invest.

72:325 (1983)), monoclonal antibody c7E3 (The EPIC Investigators, N.E. Journal of Med., 330:956 (1994)), von Willebrand factor, fibronectin, vitronectin and other ligands that have an arginine glycine-aspartic acid (RGD) sequence or other peptides or peptidomimetics that mimic this sequence (Cook, et al., *Drugs of the Future* 19:135 (1994)). Other compounds of interest include thrombin inhibitors, low molecular weight heparin, and so forth.

The particles to which the compound is attached are at least about 0.1 microns and not more than about 20 microns. In one embodiment the particles are about 0.1 microns to about 10 microns. In another embodiment the particles are at least about 1 micron and less than about 8 microns. The particles can be virtually any shape, but are generally spherical with uniform diameters. The particle may have any density, but preferably of a density approximating water, generally from about 0.7 to about 1.5 g/ml. The particles may or may not have a charge on the surface, either positive or negative, preferably negative. The particles are functionalized or functionalizable so as to covalently bind or attach such members at their surface, either directly or indirectly.

The particles may be solid (e.g., comprised of organic and inorganic polymers or latex), oil droplets (e.g., hydrocarbon, fluorocarbon, silicon fluid), or vesicles (e.g., synthetic such as phospholipids or natural such as cells and organelles). The solid particles are normally polymers, either addition or condensation polymers, which are readily dispersible in a liquid medium. Examples of suspendable particles are polymeric materials such as latex, lipid bilayers, oil droplets, cells and hydrogels. Other particle compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, poly(vinyl butyrate), polysaccharides such as dextrans and modified dextrans, etc.; either used by themselves or in conjunction with other materials. The solid particles can be comprised of polystyrene, polyacrylamide, homopolymers and copolymers of derivatives of acrylate and methacrylate, particularly esters and amides, silicones and the like.

As mentioned above, the compound is coated on the particles. Usually, the compound is covalently attached to particles. Such covalent attachment can be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). Briefly, as mentioned above, the surface of the particle may be polyfuctional or be capable of being polyfunctionalized. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature (see above). The attachment of the side member may be directly by a bond or indirectly through the intermediacy of a linking group. The length of a linking group may vary widely, depending upon the nature of the side member and of the particle.

The ratio of molecules of compound to particle is controlled in the attachment of the molecules of compound to the particle. In one approach the number of functionalized sites on the surface of the particle may be controlled by adjusting the number of such sites introduced on the surface of the particle. Alternatively, or in conjunction with the above, the ratio of molecules of compound to particle may be controlled by adjusting the concentration of the compound in the reaction medium for the attachment. Other approaches will be suggested to one skilled in the art in view of the above teaching.

The particle reagent employed in the present invention may be treated with a sufficient amount of material to block areas of adsorption on the particles. Such materials will not affect the functioning of the particles for their intended purpose in the present invention. The blocking materials include proteins such as bovine serum albumin, bovine gamma globulin, etc., polysaccharides such as dextran, etc., and the like. In another approach, which may be utilized in conjunction with the above, particles are employed wherein the number of functionalized sites for attachment substantially reduce the adsorption area on the surface of the particles.

The particles usually comprise a label, either attached thereto or incorporated therein. The label may be any moiety that may be used for the purpose of detection. The label is often a member of a signal producing system. The label is capable of being detected directly or indirectly. The label can be isotopic or nonisotopic, usually non-isotopic, and can be a dye, fluorescent molecule, chemiluminescent molecule, a catalyst, such as an enzyme, a polynucleotide coding for a catalyst, promoter, coenzyme, enzyme substrate, radioactive group, a small organic molecule, amplifiable polynucleotide sequence, and so forth.

In one specific embodiment of the present invention, the particles contain one or more dyes that absorb in the infrared. Such dyes include bacteriochlorin, bacteriochlorophytin, meropolymethine dyes, benzoannulenes, vinylogous porphorins, polymethine dyes, cyanines and merocyanines, and the like. Specific dyes of interest are Copper(II)-tetra-tert-butyl-tetrakis(dimethylamino)-29H-31H-phthalocyanine and Vanadyl-tetra-tert-butyl-tetrakis(dimethylamino)-29H-31H-phthalocyanine. The particular dye that is selected is one of convenience, availability, stability, compatibility with the particle and the like. These dyes may be incorporated directly into the particle itself, through polymerization or passive adsorption. The dyes may be loaded individually (i.e., sequentially) or in combination (i.e., simultaneously). Alternatively, the dyes may be linked to the bead in combination with the linking component, such that they do not leach from the surface. Irrespective of the loading method used, the conditions are such that the particle surface is unaffected with respect to the ability to agglutinate under appropriate conditions.

The dyes absorb light in the range of about 750 nm-900 nm, particularly in the range of about 750-850 nm. For samples with high levels of red blood cells, the light is at about 800 nm±10 nm, which is the isobestic point for oxyhemoglobin and reduced hemoglobin. The amount of dye employed with the particles varies with the extinction coefficient of the dye in the light range of interest, the required sensitivity of the assay, the size of the particles, the mode of binding of the dye to the particles, compatibility of the dye with the particle matrix, and the like. Usually, the amount of dye incorporated is in the range of about 1 to 20 weight percent, more usually 5 to 15 weight percent. Dyes which find a particular use in the present invention are phthalocyanines. Metal free phthalocyanines absorb at approximately 700 nm (e=162,000). The metal complexes shift the absorption to either shorter or longer wavelength, most metals shift the absorption to a much shorter wavelength, but some, such as lead absorb at much longer wavelength than the metal free phthalocyanines.

The complexes formed between transition metals and phthalocyanines (metollophthalocyanines and Metallonaphthalocyanines) are chemically very stable to light and heat. They are formed by condensation of opthalodinitriles in the presence of an appropriate metal. Some of the metals used in the formation of the metalophthalocyanines besides the copper (Cu) and the Vanadium (V) are magnesium (Mg), zinc (Zn), and cobalt (Co).

In one specific embodiment of the invention carboxylated microparticles with a flat absorption maximum are employed. These microparticles are prepared by incorporating multiple dyes that have distinct absorption maximum close to 805 nm. This results in a flat maximum absorption spectrum across a broad range wavelength from 780-820 nm.

The sample may be any solution, synthetic or natural, to be analyzed where the sample has been subject to an effect from a P2Y12 antagonist, particularly, a thienopyridine, potentially in combination with aspirin. The term sample includes biological tissue, including body fluids, from a host, and so forth. The sample can be examined directly or may be pretreated, usually. The present invention has particular application to samples that comprise platelets, including body fluids such as, for example, whole blood, platelet-containing blood fractions such as plasma, and the like. In one embodiment the invention has particular application to whole blood samples. The amount of the sample depends on the nature of the sample. For fluid samples such as whole anticoagulated blood, the amount of the sample is usually about 30 µl to 5000 µl, preferably, about 100 to 300 µl. The term "sample" includes unprocessed samples directly from a patient or samples that have been pretreated and prepared in any convenient liquid medium, usually an aqueous medium (e.g., sodium citrate).

Preferably, the medium for conducting the assays in accordance with the present invention is an aqueous medium. Other polar cosolvents may also be employed in the medium, usually oxygenated organic solvents of from 1-6, more usually from 1-4 carbon atoms, including alcohols, ethers and the like. Usually, such cosolvents are present in less than about 70 weight percent, more usually, in less than about 30 weight percent. Additionally, various ancillary materials are frequently employed in the method in accordance with the present invention. For example, buffers are normally present in the assay medium, as well as stabilizers for the assay medium and the assay components; surfactants, particularly non-ionic surfactants; binding enhancers, e.g., polyalkylene glycols; or the like.

The pH for the medium is usually in the range of about 2 to about 11, preferably, about 4 to about 9. Various buffers may be used to achieve the desired pH and maintain the pH during the method. Illustrative buffers include HEPES, borate, phosphate, carbonate, Tris, barbital, and the like. The particular buffer employed is not critical to the method but one buffer may be preferred over others in certain circumstances. In some circumstances HEPES is preferred and is present at a concentration of about 0.05M to about 0.001M but generally at a concentration of about 0.01M.

The volume of assay medium is about 25 to about 500 microliters, usually about 75 to about 250 microliters. The assays may be carried out in any suitable container. Conveniently, the container is a cuvette or cartridge that is used with the instrument for carrying out the assay and measuring the assay results. The reaction container usually contains the activation initiator in accordance with the present invention in dry lyophilized form together with other reagents such as the particle reagent and the like, stabilizers and so forth.

The combination of sample and particle reagent is incubated under conditions for agglutinating the particles. Moderate temperatures are normally employed for carrying out the method. The temperature may be constant or may vary. Usually, a constant temperature is employed during the reaction step. The temperature employed is usually about 10 to about 80° C., more usually, about 15 to about 45° C., preferably, the temperature should be at least 25° C., more preferably in the range of about 30 to about 40° C., usually about 37° C.

The extent of agglutination of the particles is determined and is related to the presence and/or amount of the member in the sample. The presence of agglutination may be determined visually by observing clumping of the particles, which would indicate agglutination. Preferably, as mentioned above, the particles may be colored to aid in visualizing agglutination or clumping of the matrix. The extent of agglutination may be measured spectrophotometrically, turbidimetrically, nephelometrically, etc., by observing the rate of change of optical density of the medium, and so forth.

In a specific embodiment of the present invention an assay for platelet function activity is conducted on a whole blood sample from a patient undergoing treatment with a thienopyridine. The sample is combined in a suitable container, e.g., reaction cuvette, with fibrinogen coated particles, and the composition of ADP and PGE1 to form an assay medium. The particles of the particle reagent have one or more infrared dyes incorporated therein. The combination is subjected to agglutination conditions. Then, the medium is irradiated with light in the infrared region. The transmission of infrared light from the assay mixture is determined where the level of transmission is related to platelet function activity.

The agglutination medium is selected to have high absorption at ~800 nm. The ratio between the agglutination medium absorption coefficient and whole blood absorption coefficient should preferably be greater than about 4:1 at 800 nm. The absorption ratio for a particular assay is a function of both the absorption coefficient of the agglutination medium and the concentration of the agglutination medium in the assay sample.

After the sample has been combined with the reagents, desirably it will be heated to a temperature above room temperature, but below that which would interfere with the assay, so as to insure that the temperature can be controlled without adversely affecting the assay result. Desirably, the temperature should be at least 25°, preferably in the range of 30-40° C., more preferably about 37° C. The reaction medium is usually gently agitated upon combining of the reagents with the sample and during the period of the reaction. Agitation is sufficient to achieve and maintain homogeneity in the assay samples. The total time of the readings from the zero time (time of mixing), may range from about 10 sec. to 10 min., more usually about 30 sec. to 8 min., and preferably about 30 sec. to 3 min. The data may be analyzed by any convenient means, particularly using an algorithm that can manipulate the data in relation to calibrators and/or controls.

The level of agglutination is an indication of the platelet function activity of the sample tested. The level of agglutination may be compared against a standard of known platelet function activity. Usually, the result will be compared to a calibrator, which may be performed concomitantly or have been performed previously or may be provided as a standard curve.

The method of the present invention may be employed in conjunction with an assay for platelet count such as that described in U.S. patent application Ser. No. 09/177,884 filed Oct. 23, 1998 (the '884 application), the relevant disclosures of which are incorporated herein by reference.

The above assays preferably may be conducted in a device, which allows the reactions in accordance with the present invention to occur and which measures the results thereof. The instrument should assess platelet function based upon the ability of activated platelets to bind fibrinogen. As activated platelets bind and agglutinate fibrinogen-coated particles, there is an increase in light transmittance. In general, an instrument to measure the result of the assay is one that can measure agglutination. Preferably, the instrument measures a change in optical signal due to agglutination. Suitable instruments include, by way of illustration and not limitation a kinetic spectrophotometer, ULTEGRA System ® instrument (commercially available from Accumetrics, San Diego, Calif. and employed for rapid platelet function activity measurements on normal samples), or the like.

The ULTEGRA® System instrument is a turbidometric based optical detection system, that measures platelet induced aggregation as an increase in light transmittance. The system consists of an analyzer, disposable cartridge and controls. The cartridge contains reagents based on microparticle agglutination technology. The quality control system includes an electronic control, two levels of assayed "wet" controls (WQC), an in-cartridge humidity sensor, an in-packaging temperature indicator, and a test for concurrence of two assay channels. The analyzer controls assay sequencing, establishes the assay temperature, controls the reagent-sample mixing for the required duration, determines the degree of platelet function, displays the result and performs self-diagnostics. For use in the present methods the test cartridge of the system contains a lyophilized preparation comprising particles with covalently attached GPIIb/IIIa receptor ligand, a composition of ADP and PGE1, and buffer. The patient sample is usually citrated whole blood, which is automatically dispensed from the blood collection tube into the cartridge by the analyzer, with no blood handling required by the user. The interaction is monitored by the infrared absorbency characteristics of the particles. As the particles interact with the platelets, the agglutination of the particles is measured through the optical system of the ULTEGRA™ analyzer. The agglutination is detected as an increase in the transmission of infrared light through the sample. The reaction kinetics are analyzed and translated into "P2Y12 Response Units", PRU.

In another embodiment of the present invention is a kit that includes in packaged combination a lyophilized preparation comprising particles with covalently attached fibrinogen, composition of ADP and PGE1, and buffer. The lyophilized preparation may be present in a reaction container such as a cartridge used in the instrument of analysis. For the aforementioned ULTEGRA® System, the lyophilized preparation may be placed in the outer wells of the four-well cartridge used in the analyzer. The kit may also include a sample collection container and/or a device for carrying out the present method. The relative amounts of reagents may be varied widely to provide for concentrations in solution of the reagents that substantially optimize the sensitivity of a determination.

Where appropriate, the reagents can be placed in an airtight package in order to maintain the activity of any reagents. The package may be, for example, a bag, pouch, or the like fabricated from a material that is substantially non-permeable to moisture. Such materials include, by way of example and not limitation, plastic, aluminum foil, and the like. For blood samples the kit may also include an article for piercing a person's skin, disinfectant or sterilizing pads and so forth. The kit may also include calibrators and standards. Furthermore, the kit may also include one or more reagents for conducting an assay for platelet count.

The kit can include the reagents necessary for carrying out the assay of the present invention. In one embodiment, the kit includes a blood vial, a buffer that maintains the pH and salt concentration of the blood sample assessed within ranges suitable for platelet mediated agglutination of the solid surface and small polymeric beads coated with platelet GPIIb/IIIa receptor ligand. The buffer can be in solution, or can consist solely of the buffering composition and salts to which a known amount of water is added to give the desired buffer solution. Optionally, the kit can also comprise an anticoagulant. In one embodiment, the buffer is HEPES; the anticoagulant is citrate; a GPIIb/IIIa receptor ligand is fibrinogen; small polymeric beads are polyacrylonitrile or carboxylated polystyrene in which a peptide GPIIb/IIIa receptor ligand, such as fibrinogen, is covalently bonded to the bead surface by means of a covalent bond between the N-terminus of the peptide and an N-hydroxysuccinimide or carboxylate group on the bead surface in a further embodiment, the kit additionally comprises a platelet activator, such as a composition of ADP and PGE1.

EXAMPLE

The following examples are offered by way of illustration and without limitation. Parts and percentages are by weight unless otherwise indicated The following examples and preparations are intended to illustrate the invention but are not intended to limit its scope.

Dose response testing was performed with ADP (Chronolog) and PGE1(SIGMA) at 20 µM and 22 nM final concentrations respectively. ADP was diluted in Hepes/Saline, pH 7.4 buffer to a final concentration of 200 µM prior to use on the aggregometer. PGE1 was diluted in Hepes/Saline, pH 7.4 buffer to a final concentration of 220 nM prior to use on the aggregometer. A P2Y12 receptor blocker was diluted in DMF to final concentrations of 1 mM, 2 mM and 5 mM.

Five microliters of the diluted P2Y12 compound were spiked into 5 mL whole blood. Samples were inverted and incubated for one hour at room temperature. The whole blood baseline sample did not receive any additive. Once incubation was complete, whole blood samples were spun at 1500 rpm for 15 minutes for platelet rich plasma (PRP) and 3500 rpm for 15 minutes for platelet poor plasma (PPP). Platelet count was adjusted to approximately 250,000/µL for each sample using PPP.

For aggregometry, 450 µL of adjusted PRP was added to the glass cuvette. The blank sample contained 450 µL PPP and 50 µL Hepes/Saline buffer. Fifty microliters of a composition of 200 µM ADP and 220 nM PGE1 was added to each PRP sample and tested for ten minutes on the aggregometer.

Results

Figure 2:
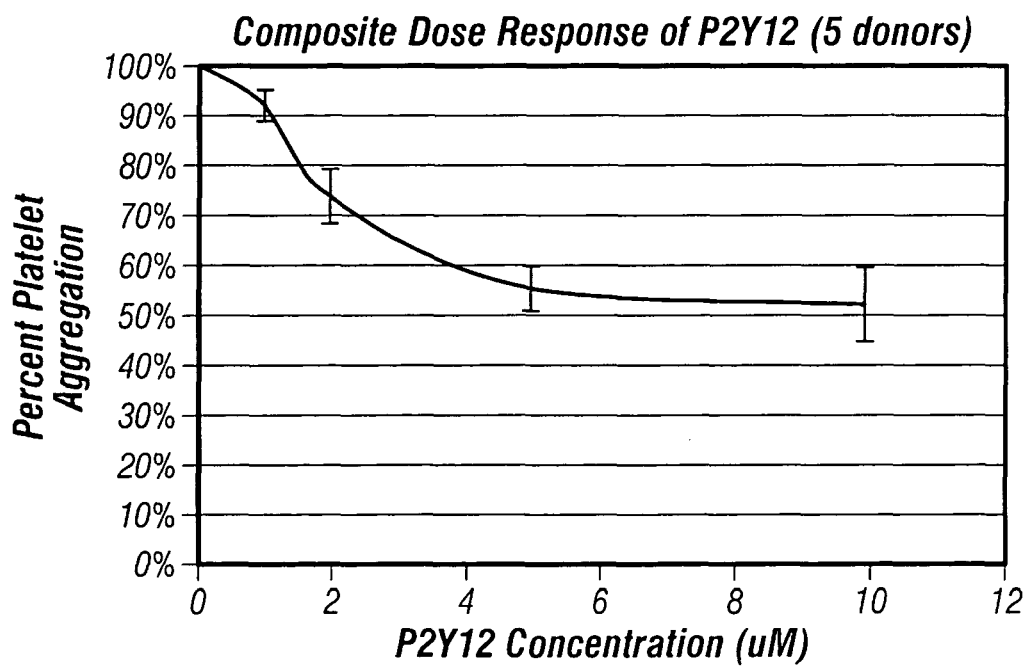
FIG. 2 illustrates the mean response of five individuals.
Figure 3:
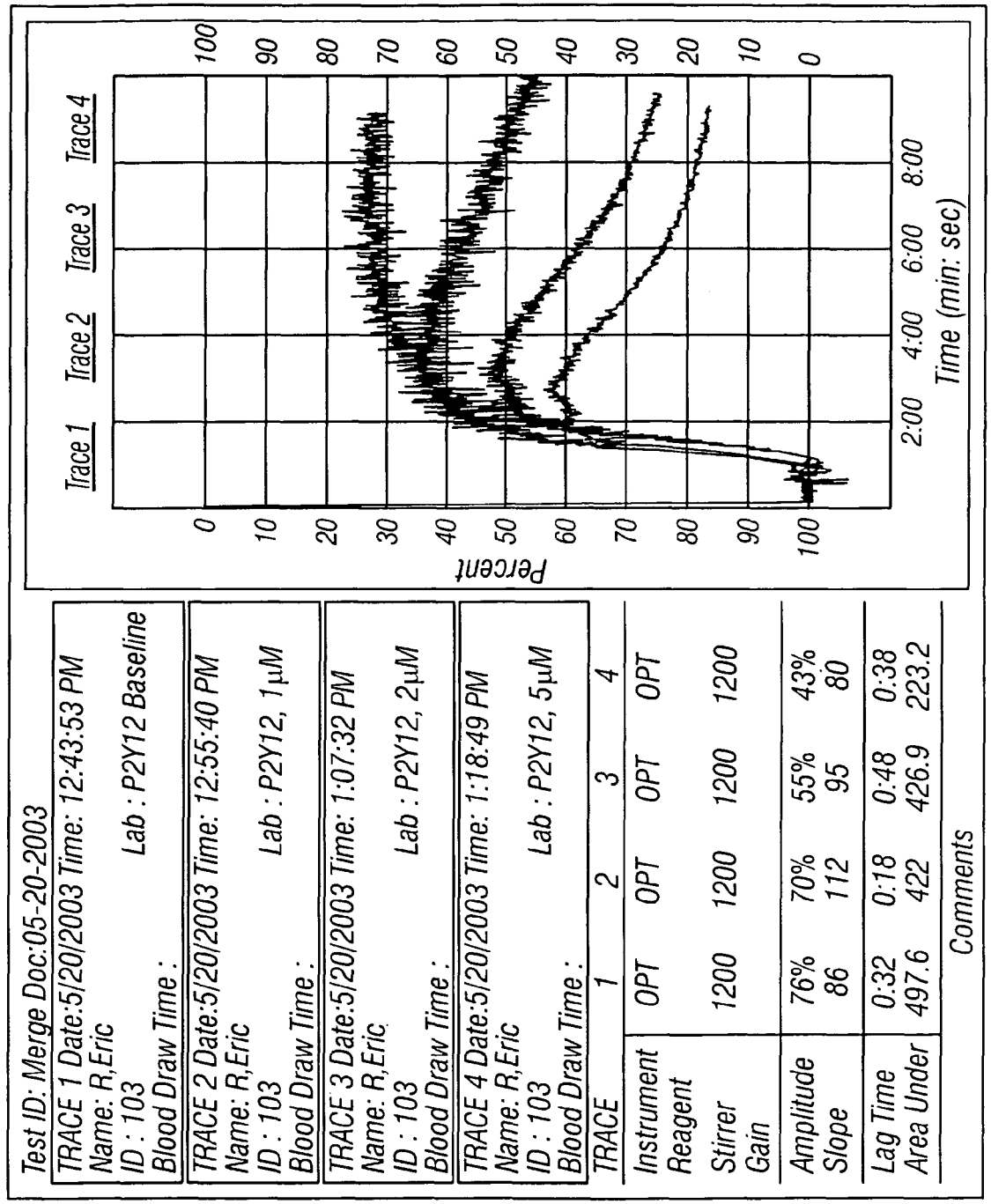
FIG. 3 illustrates the extent of platelet aggregation from a blood sample treated with the antagonist of the present invention.

As illustrated in FIG. 3, the above reagents and system successfully detects the extent of platelet aggregation from a blood sample treated with an P2Y12 antagonist. FIGS. 1 and 2 illustrates the mean response of one individual and five individuals, respectively.

It is evident from the above results illustrated in FIG. 3 that a simple, rapid method is provided by the present invention for conducting an assay for platelet activity on samples that have been affected by exposure to a P2Y12 antagonist.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for measuring inhibition of platelet aggregation by a P2Y12 antagonist, comprising the steps of:
   a) providing a platelet containing blood sample from an individual treated with a P2Y12 antagonist;
   b) contacting said platelet containing blood sample with particles comprising an attached GPIIb/IIIa receptor ligand, adenosine diphosphate (ADP) and prostaglandin E1 (PGE1) under conditions suitable for agglutination of said particles mediated by said platelet in said blood sample, wherein said ADP has a final concentration of 2 to 35 µM and said PGE1 has a final concentration of 2 to 30 nM; and
   c) assessing said agglutination to determine the level of inhibition of platelet aggregation by said P2Y12 antagonist in said individual, wherein a reduced level of agglutination indicates whether said individual has reduced ability to form platelet aggregation in response to said P2Y12 antagonist treatment.

2. The method of claim 1, wherein said P2Y12 antagonist is a thienopyridine.

3. The method of claim 2, wherein said thienopyridine is clopidogrel.

4. The method of claim 2, wherein said thienopyridine is ticlopidine.

5. The method of claim 1, wherein said platelet containing blood sample is from an individual treated with a P2Y12 antagonist and aspirin.

6. The method of claim 1, wherein said particles comprise polystyrene or latex.

7. The method of claim 1, wherein said particles comprise an infrared dye, the contact between the platelet containing blood sample and the particles forms an assay mixture, the agglutination of said particles mediated by said platelet is assessed by irradiating said assay mixture with a light in the infrared spectrum, and assessing the transmission of infrared light from said assay mixture.

8. The method of claim 1, wherein said GPIIb/IIIa receptor ligand comprises a substance selected from the group consisting of fibrinogen, monoclonal antibody 10E5, monoclonal antibody c7E3, von Willebrand factor, fibronectin, vitronectin, a ligand that has an arginine glycine-aspartic acid (RGD) sequence, and a peptide or a peptidomimetic that mimics RGD sequence.

9. The method of claim 1, wherein said GPIIb/IIIa receptor ligand is fibrinogen.

10. The method of claim 1, wherein said ADP has a final concentration of 15 to 20 µM.

11. The method of claim 1, wherein said PGE1 has a final concentration of 20 to 25 nM.

12. The method of claim 1, which is conducted at a temperature ranging from 30° C. to 40° C., and the total time of the readings from the time of the contact among the platelet containing blood sample, the particles comprising an attached GPIIb/IIIa receptor ligand, ADP and PGE1 ranges from about 10 seconds to about 10 minutes.

13. The method of claim 1, wherein said platelet containing blood sample is a whole blood sample.

14. The method of claim 1, wherein said platelet containing blood sample is a plasma sample.

15. The method of claim 14, wherein said plasma sample is a platelet rich plasma (PRP) sample.

16. The method of claim 1, wherein said particles, ADP and PGE1 are contained in an assay medium.

17. The method of claim 16, wherein said particles, ADP and PGE1 are contained in an assay medium on a disposable cartridge.

18. The method of claim 16, wherein said assay medium has an absorption peak at about 800 nm.

* * * * *